United States Patent
Duan et al.

(10) Patent No.: US 8,088,349 B2
(45) Date of Patent: Jan. 3, 2012

(54) CLEAN METHOD FOR PREPARING LAYERED DOUBLE HYDROXIDES

(75) Inventors: Xue Duan, Beijing (CN); Dianqing Li, Beijing (CN); Zhi Lv, Beijing (CN); Yanjun Lin, Beijing (CN); Xiangyu Xu, Beijing (CN)

(73) Assignee: Beijing University of Chemical Technology, Beijing (CN)

( * ) Notice: Subject to any disclaimer, the term of this patent is extended or adjusted under 35 U.S.C. 154(b) by 433 days.

(21) Appl. No.: 11/853,788

(22) Filed: Sep. 11, 2007

(65) Prior Publication Data
US 2008/0170978 A1   Jul. 17, 2008

(30) Foreign Application Priority Data

Jan. 12, 2007 (CN) .......................... 2007 1 0062650

(51) Int. Cl.
*C01F 11/20* (2006.01)

(52) U.S. Cl. ...................... 423/306; 423/327.1; 423/331; 423/395; 423/399; 423/420.2; 423/463; 423/464; 423/465; 423/554; 423/555; 423/558; 423/594.1; 423/594.2; 423/594.3; 423/594.4; 423/594.5; 423/594.6; 423/594.8; 423/594.14; 423/594.16; 423/595; 423/596; 556/28; 556/31

(58) Field of Classification Search .................. 423/306, 423/327.1, 331, 395, 399, 420.2, 463, 464, 423/465, 554, 555, 558, 594.1, 594.2, 594.3, 423/594.4, 594.5, 594.6, 595, 596, 594.8, 423/594.14, 594.16; 556/28, 31
See application file for complete search history.

(56) References Cited

U.S. PATENT DOCUMENTS 6,652,828 B2 * 11/2003 Stamires et al. ........... 423/593.1

FOREIGN PATENT DOCUMENTS

WO    WO 2007/051377 A1    7/2006

OTHER PUBLICATIONS (Y. Zhao, F. Li, R. Zhang, D.G. Evans, X. Duan, Preparation of layered double-hydroxide nanomaterials with a uniform crystallite size using a new method involving separate nucleation and aging steps, Chem. Mater., 2002, 14:4286-4291).
Zhi Ping Xu, Guo Qing (Max) Lu, Hydrothermal Synthesis of Layered Double Hydroxides (LDHs) from Mixed MgO and $Al_2O_3$: LDH Formation Mechanism, *Chem. Mater.* 2005, 17:1055-1062.
Wei Jiang, LanPing Nong, WenLing Lai, ZeYu Chen, Intercalation and assembly of organic acid radical-pillared layered double hydroxides by calcination-rehydration, Chemical Research and Application, 2004, 16(6): 828-830.
Jiang Wei, et al, "Intercalation and Assembly of Organic Acid Radical-Pillared Layered", Chemical Research and Application, 2004, 16(6): 828-830.

* cited by examiner

*Primary Examiner* — Stuart Hendrickson
(74) *Attorney, Agent, or Firm* — Blakely, Sokoloff, Taylor & Zafman LLP.

(57) ABSTRACT

Disclosed is a clean method for preparing layered double hydroxides (LDHs), in which hydroxides of different metals are used as starting materials for production of LDHs by atom-economical reactions. The atom efficiency of the reaction is 100% in each case because all the atoms of the reactants are converted into the target product since only $M^{2+}(OH)_2$, $M^{3+}(OH)_3$, and $CO_2$ or $H_nA^{n-}$ are used, without any NaOH or other materials. Since there is no by-product, filtration or washing process is unnecessary. The consequent reduction in water consumption is also beneficial to the environment.

4 Claims, 2 Drawing Sheets

CLEAN METHOD FOR PREPARING LAYERED DOUBLE HYDROXIDES

CROSS-REFERENCE TO RELATED APPLICATIONS

The present patent application claims priority from Chinese Patent Application No. 200710062650.9, filed on Jan. 12, 2007.

TECHNICAL FIELD

The present invention relates to a clean method for preparing layered double hydroxides, and belongs to the field of synthesis of inorganic nonmetallic functional materials.

TECHNICAL BACKGROUND

Layered double hydroxides (LDHs), which belong to a typical family of anionic layered materials, can be represented by the general formula $[M^{2+}_{1-x}M^{3+}_x(OH)_2]^{x+}(A^{n-})_{x/n} \cdot mH_2O$, where $M^{2+}$ is a bivalent metal cation, $M^{3+}$ is a trivalent metal cation, $A^{n-}$ denotes an interlayer anions with negative charge n, m is the number of interlayer water molecules, and x is the molar ratio of the $M^{3+}$ to the sum of the $M^{3+}$ and $M^{2+}$. The identity and ratio of the layer elements as well as the interlayer guest anions can be adjusted over a wide range in order to obtain materials with specific structures and properties. Because of their flexible composition and versatility, LDHs have been widely investigated for their potential applications in the fields of catalysis, adsorption, ion exchange and functional materials.

LDHs are traditionally synthesized by coprecipitation methods, hydrothermal methods, ion-exchange methods or calcination-rehydration methods. A large amount of sodium salt is produced as by-product during the preparation of LDHs by traditional methods. The sodium salt mother liquor is always discharged directly due to the high energy costs of evaporation, and thus leads to environmental pollution. In addition, the use of strong alkali in the synthesis process means that the product must be well washed with water (tens or even hundred times of the product's mass), which leads to significant waste of water and problems with treatment of the alkaline effluent. Thus it is necessary to develop an environmentally friendly technology for preparation of LDHs.

The coprecipitation method is the most popular method used to prepare LDHs. A mixed salt solution containing the metal ions which constitute the layers are coprecipitated with alkali in order to obtain the LDHs. Either the mixed salt solution or the alkali solution can contain the corresponding interlayer anionic group. In a related reference (Y. Zhao, F. Li, R. Zhang, D. G. Evans, X. Duan, Preparation of layered double-hydroxide nanomaterials with a uniform crystallite size using a new method involving separate nucleation and aging steps, Chem. Mater., 2002, 14:4286-4291), a method for synthesis of LDHs has been reported, in which LDHs are prepared by coprecipitation of a mixture of soluble salts of bivalent and trivalent metal ions with $Na_2CO_3$ and NaOH. However, in this method, large quantity of water is required to wash the product after the reaction, due to the large amount of sodium salts produced in the reaction and the strongly alkaline solution, and a significant waste of water is thus caused.

The hydrothermal method for preparation of LDHs is a method in which insoluble oxides or hydroxides containing the metal ions to be incorporated in the layers are treated with water at a high temperature under a high pressure. In this method, $Na_2CO_3$ or $NaHCO_3$ is generally used as main starting materials, and the sodium salt formed as a co-product needs be removed by washing which causes a lot of water waste. In a related reference (Zhi Ping Xu, Guo Qing (Max) Lu, Hydrothermal Synthesis of Layered Double Hydroxides (LDHs) from Mixed MgO and $Al_2O_3$: LDH Formation Mechanism, Chem. Mater. 2005, 17:1055-1062), a process for preparing MgAl—$CO_3^{2-}$-LDHs has been reported, in which $Na_2CO_3$ or $NaHCO_3$ is added into a mixture of MgO and $Al_2O_3$ at 110° C., and the product contains a lot of $Na^+$ which needs to be washed with large quantity of water.

The ion-exchange method is used when $M^{2+}$ and $M^{3+}$ are not stable in alkaline medium or no suitable soluble salt of the anion $A^{n-}$ can be found. An LDHs precursor is first synthesized and the ion-exchange reaction is then carried out in the presence of the required interlayer anions under appropriate conditions in order to prepare the target LDHs. In this method, the washing process cannot be omitted due to the formation of salt by-products in the production of the precursor. WO 2007/051377A1 discloses a method for preparing LDHs with interlayer organic anions containing double bonds, in which an LDHs precursor containing interlayer $NO_3^-$ anions is first synthesized by the coprecipitation method, and after washing and filtration, LDHs containing organic anions containing double bonds is obtained by the ion-exchange process.

In the calcination-rehydration method, complex metal oxides (LDO) are obtained by calcination of an LDHs precursor, and the LDO is added into a solution containing the desired anions to restore or partly restore the ordered layered structure of LDHs. Generally, it is possible to restore the ordered layered structure when the calcination temperature is below 500° C. When the calcination temperature exceeds 600° C., a spinel phase is formed from which the layer structure of the LDHs cannot be restored. An LDHs precursor must also be synthesized for use in the calcination-rehydration method and therefore the washing process cannot be omitted due to the formation of salt by-products. In a related reference (Wei Jiang, LanPing Nong, WenLing Lai, ZeYu Chen, Intercalation and assembly of organic acid radical-pillared layered double hydroxides by calcination-rehydration, Chemical Research and Application, 2004, 16(6): 828-830), LDHs with anions of myristic acid or stearic acid as the interlayer anion were prepared by synthesizing MgAl-LDHs and ZnAl-LDHs precursors with the coprecipitation method, calcinating the precursors to obtain LDO, and then putting LDO in myristic acid or stearic acid solution. In the process of preparing the precursors, a large amount of by-product is formed and large quantity of water is required for washing.

SUMMARY OF THE INVENTION

An object of this invention is to provide a clean method for preparing layered double hydroxides. In this method, $M^{2+}(OH)_2$, $M^{3+}(OH)_3$, and $CO_2$ or $H_nA^{n-}$ are used as starting materials to produce LDHs by atom-economical reactions.

Most metal hydroxides have low solubility product constants and are difficult to dissolve in water. Their solubility increases at high temperatures and pressures. The resulting solution of metal cations can co-precipitate with $CO_3^{2-}$ or other anions, giving layered double hydroxides with the required interlayer anion. The reaction can be represented by the following overall equation:

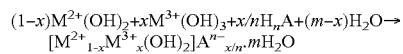

Only $M^{2+}(OH)_2$, $M^{3+}(OH)_3$, and $CO_2$ or $H_nA^{n-}$ are used in this method. Use of NaOH or other materials has been avoided. All the atoms of the reactants are incorporated into the target product. Therefore the atom efficiency of this reaction is 100% which is a typical atom-economical reaction. In addition, the process of washing and filtration can be omitted because there is no by-product, such that the environment can be protected and water resource is also saved.

The preparation method of LDHs provided in the present invention includes the following steps:

A. Hydroxides of $M^{2+}$ and $M^{3+}$ (with a molar ratio of $M^{2+}/M^{3+}$=2~4) are added into water (the weight ratio of $H_2O$ to the hydroxides being 0.25~999) to obtain a mixture, and the mixture is then added into a reactor, wherein $M^{2+}$ represents one or two divalent cations selected from $Mg^{2+}$, $Zn^{2+}$, $Ca^{2+}$, $Cu^{2+}$, $Ni^{2+}$, $Co^{2+}$, $Fe^{2+}$, $Mn^{2+}$, $Cd^{2+}$, and $Be^{2+}$, of which $Mg^{2+}$, $Zn^{2+}$, $Ca^{2+}$, and $Ni^{2+}$ are preferable; $M^{3+}$ represents one or two trivalent cations selected from $Al^{3+}$, $Co^{3+}$, $Fe^{3+}$, $Mn^{3+}$, $Cr^{3+}$, $V^{3+}$, $In^{3+}$, and $Ga^{3+}$, of which $Al^{3+}$ and $Fe^{3+}$ are preferable.

B. $CO_2$ is fed into the reactor in such an amount that the molar ratio of $CO_2/M^{3+}$=1-70, or $H_nA^n$ (with the molar ratio of $M^{3+}/A^{n-}$=n) is added into the reactor, and then the contents in the reactor are reacted for 0.1-10 days to obtain a layered double hydroxide with $CO_3^{2-}$ or $A^{n-}$ as the intercalated anion.

In the above step B, $CO_2$ can be added into the reactor in a form of gas or dry ice, and the molar ratio of $CO_2/M^{3+}$ is preferably 2~20.

In the above step B, $H_nA^n$ is an acid containing any of the following anions: (1) inorganic anions: $F^-$, $Cl^-$, $Br^-$, $I^-$, $NO_3^-$, $ClO_3^-$, $ClO_4^-$, $IO_3^-$, $H_2PO_4^-$, $CO_3^{2-}$, $S_3^{2-}$, $S_2O_3^{2-}$, $HPO_4^{2-}$, $WO_4^{2-}$, $CrO_4^{2-}$, $PO_4^{3-}$ and so on; (2) organic anions: terephthalate, adipate, succinate, dodecyl sulfonate, p-hydroxybenzoate, benzoate and so on; and (3) isopolyacid and heteropolyacid anions: $Mo_7O_{24}^{6-}$, $V_{10}O_{28}^{6-}$, $PW_{11}CuO_{39}^{6-}$, $SiW_9V_3O_{40}^{7-}$. Among them, $Cl^-$, $NO_3^-$, $CO_3^{2-}$, $SO_3^{2-}$, $PO_4^{3-}$, terephthalate, succinate, benzoate and $Mo_7O_{24}^{6-}$ are preferred.

The reactor may be a rector fitted with a reflux device, or an airtight reactor fitted with a churn-dasher. In case of the rector fitted with a reflux device, the reaction was carried out for 1~10 days. In case of the airtight reactor, the reaction was carried out at a temperature of 100~300° C. and a pressure of 0.1~10 MPa for 0.1~3 days.

The obtained layered double hydroxide may be filtered directly after the reaction and dried at 70° C.

According to the powder XRD pattern, infrared spectra, and elemental analysis, the chemical composition of the product can be determined as $[M^{2+}_{1-x}M^{3+}_x(OH)_2]A^{n-}_{x/n} \cdot mH_2O$, wherein $M^{2+}$ is one or two selected from $Mg^{2+}$, $Zn^{2+}$, $Ca^{2+}$, $Cu^{2+}$, $Ni^{2+}$, $Co^{2+}$, $Fe^{2+}$, $Mn^{2+}$, $Cd^{2+}$, and $Be^{2+}$;

$M^{3+}$ is one or two selected from $Al^{3+}$, $Co^{3+}$, $Fe^{3+}$, $Mn^{3+}$, $Cr^{3+}$, $V^{3+}$, $In^{3+}$, and $Ga^{3+}$;

$H_nA^n$ is an acid containing any of the following anions: (1) inorganic anions: $F^-$, $Cl^-$, $Br^-$, $I^-$, $NO_3^-$, $ClO_3^-$, $ClO_4^-$, $IO_3^-$, $H_2PO_4^-$, $CO_3^{2-}$, $SO_3^{2-}$, $S_2O_3^{2-}$, $HPO_4^{2-}$, $WO_4^{2-}$, $CrO_4^{2-}$, $PO_4^{3-}$ and so on; (2) organic anions: terephthalate, adipate, succinate, dodecyl sulfonate, p-hydroxybenzoate, benzoate and so on; and (3) isopolyacid and heteropolyacid anions: $Mo_7O_{24}^{6-}$, $V_{10}O_{28}^{6-}$, $PW_{11}CuO_{39}^{6-}$, and $SiW_9V_3O_{40}^{7-}$. Among them, $Cl^-$, $NO_3^-$, $CO_3^{2-}$, $SO_3^{2-}$, $PO_4^{3-}$, terephthalate, succinate, benzoate and $Mo_7O_{24}^{6-}$ are preferred.

x represents the molar ratio of $M^{3+}/(M^{2+}+M^{3+})$ and is in the range 0.2~0.33;

m represents the amount of crystal water and is in the range 0.2~0.33;

n represents the charge of the intercalated anions and is an integer of 1~7.

The present invention is advantageous in that all the atoms of reactants are converted into the target product and there is no by-product; the pure product can be obtained by drying the target product without washing so that a large amount of water can be saved with considerable benefit to the environment.

BRIEF DESCRIPTION OF THE ACCOMPANYING DRAWINGS

PREFERRED EMBODIMENTS FOR CARRYING OUT THE INVENTION

EXAMPLES

Example 1

MgAl—$CO_3$-LDHs were prepared as follows.

Step A: Total 10 g $Mg(OH)_2$ and $Al(OH)_3$ with a molar ratio of $Mg^{2+}/Al^{3+}$=2:1 were put into 90 g of deionized water, and the resulting mixture was transferred to a three-necked flask fitted with a reflux device.

Step B: The mixture was heated to 100° C. under stirring for four days, while $CO_2$ was fed thereto at a flow rate of 10 ml/min. The resulting slurry product was filtered and dried in air at 70° C. for 8 h to give $Mg_4Al_2(OH)_{12}CO_3 \cdot 4H_2O$.

Figure 1:
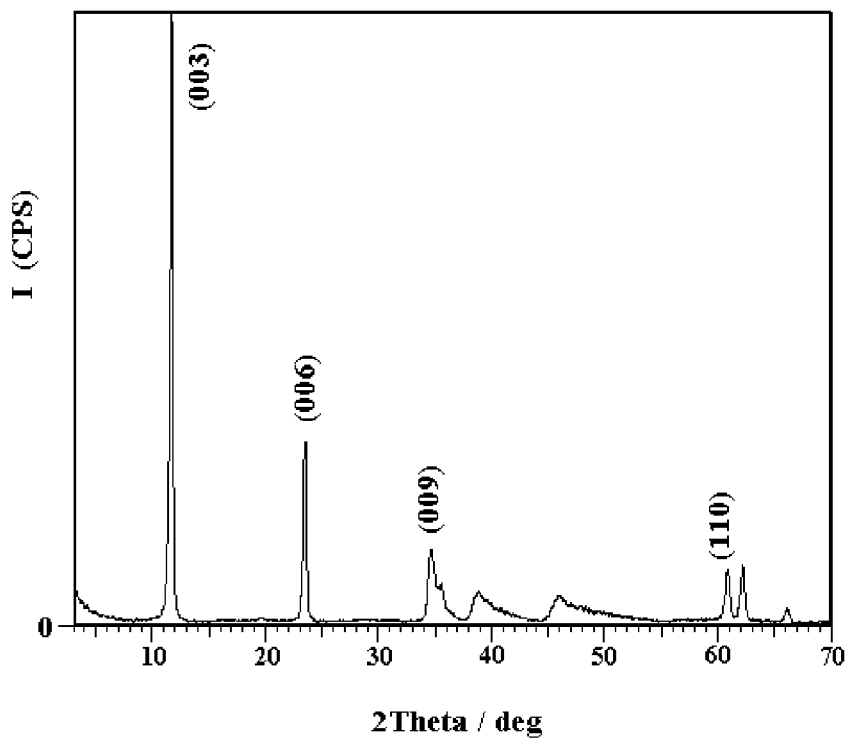
FIG. 1 shows the XRD patterns of MgAl—$CO_3$-LDHs obtained in example 1.

The powder XRD patterns of the prepared $Mg_4Al_2(OH)_{12}CO_3 \cdot 4H_2O$ were recorded using a Shimadzu XRD-6000 diffractometer, and were shown in FIG. 1. The typical peaks which correspond to the (003), (006), (009) reflections were found at 2θ=11.7°, 23.4°, 34.5°. It could be concluded from the patterns that the samples had a layered crystal structure.

Figure 2:
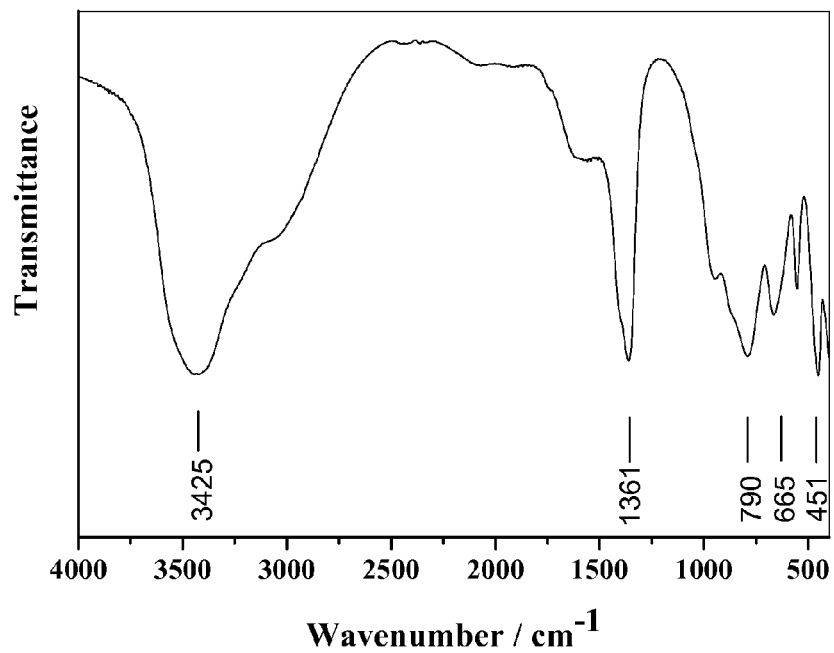
FIG. 2 shows the FT-IR spectra of MgAl—$CO_3$-LDHs obtained in example 1.

The infrared spectra of the samples, obtained using a Bruker Vector 22 model Fourier transform infrared spectrometer (FT-IR), were shown in FIG. 2. The infrared strong absorption peak at 1361 $cm^{-1}$ could be attributed to the symmetric vibration absorption of $CO_3^{2-}$, which was intercalated between the MgAl-LDH layers. No absorption peak arising from impurities were observed in FIG. 2.

Example 2

$Ni_8Fe_2(OH)_{20}(C_8H_4O_4) \cdot 4H_2O$ was prepared as follows.

Step A: Total 5 g $Ni(OH)_2$ and $Fe(OH)_3$ with a molar ratio of $Ni^{2+}/Fe^{3+}$=4:1 were put into 90 g of deionized water, and the resulting mixture was transferred to a three-necked flask fitted with a reflux device.

Step B: 0.58 g terephthalic acid was added to the flask. The contents in the flask were heated to 100° C. and reacted for eight days under stirring. After filtration and drying in air at 70° C. for 8 h, $Ni_8Fe_2(OH)_{20}(C_8H_4O_4) \cdot 4H_2O$ was obtained.

Figure 3:
FIG. 3 shows the TEM photo of $Ni_8Fe_2(OH)_{20}(C_8H_4O_4) \cdot 4H_2O$ obtained in example 2.

The TEM image of the product produced in example 2, obtained using a Hitachi S-3500N scanning electron microscope, was shown in FIG. 3. The image reveals a layered hexagonal morphology of LDHs.

Example 3

$ZnMg_3Al_2(OH)_{12}CO_3 \cdot 4H_2O$ was prepared as follows.

Step A: Total 20 g $Zn(OH)_2$, $Mg(OH)_2$ and $Al(OH)_3$ with a molar ratio of $Zn^{2+}/Mg^{3+}/Al^{3+}=1:3:2$ were put into 80 g of deionized water, and the mixture was transferred to an airtight reactor fitted with a churn-dasher.

Step B: After adding 40 g of dry ice to the reactor, the system was heated at 150° C. for one day under stirring. The resulting slurry was filtered and dried in air at 70° C. for 8 h to give $ZnMg_3Al_2(OH)_{12}CO_3.4H_2O$.

Elemental analysis of the product obtained in example 3 was performed on an ICPS-7500 inductively coupled plasma spectrometer. The molar ratio of Zn:Mg:Al was measured as 1:3:2 and no $Na^+$ was found in the product.

Example 4

$Ca_4Al_2(OH)_{12}CO_3.4H_2O$ was prepared as follows.

Step A: Total 20 g $Ca(OH)_2$ and $Al(OH)_3$ with a molar ratio of $Ca^{2+}/Al^{3+}=3:1$ were put into 80 g of deionized water, and the mixture was transferred to an airtight reactor fitted with a churn-dasher.

Step B: The system was heated to 250° C. under stirring, while carbon dioxide gas was flowed into the reactor to keep the pressure at 5 Mpa for 0.5 day. The resulting slurry was filtered and dried in air at 70° C. for 8 h to give $Ca_4Al_2(OH)_{12}CO_3.4H_2O$.

Example 5

$Mg_6Fe_3(OH)_{18}(PO_4).4H_2O$ was prepared as follows.

Step A: Total 4 g $Mg(OH)_2$ and $Fe(OH)_3$ with a molar ratio of $Mg^{2+}/Fe^{3+}=2:1$ were put into 600 g deionized water, and the mixture was transferred to an airtight reactor fitted with a churn-dasher.

Step B: 0.58 g $H_3PO_4$ was put into the reactor. The contents in the reactor were heated to 100° C. for 1.5 days under stirring. The resulting slurry was filtered and dried in air at 70° C. for 8 h to give $Mg_6Fe_3(OH)_{18}(PO_4).4H_2O$.

What is claimed:

1. A clean method for preparing layered double hydroxides comprising:

adding hydroxides of $M^{2+}$ and $M^{3+}$ with a molar ratio of $M^{2+}/M^{3+}=2\sim4$ into water to obtain a mixture in which the weight ratio of $H_2O$ to the hydroxides is 0.25~999, wherein $M^{2+}$ represents one or two divalent cations selected from $Mg^{2+}$, $Zn^{2+}$, $Ca^{2+}$, $Cu^{2+}$, $Ni^{2+}$, $Co^{2+}$, $Fe^{2+}$, $Mn^{2+}$, $Cd^{2+}$, and $Be^{2+}$, and $M^{3+}$ represents one or two trivalent cations selected from $Al^{3+}$, $Co^{3+}$, $Fe^{2+}$, $Mn^{3+}$, $Cr^{3+}$, $V^{3+}$, $In^{3+}$, and $Ga^{3+}$;

adding the mixture into a reactor;

feeding $H_nA^n$ in such an amount that the molar ratio of $M^{3+}/A^{n-}=n$ into the reactor, wherein $H_nA^n$ is an acid containing any of the following anions: (1) inorganic anions: $F^-$, $Cl^-$, $Br^-$, $I^-$, $NO_3^-$, $ClO_3^-$, $ClO_4^-$, $IO_3^-$, $H_2PO_4^-$, $CO_3^{2-}$, $SO_3^{2-}$, $S_2O_3^{2-}$, $HPO_4^{2-}$, $WO_4^{2-}$, $CrO_4^{2-}$, and $PO_4^{3-}$; (2) organic anions: terephthalate, adipate, succinate, dodecyl sulfonate, p-hydroxybenzoate, and benzoate; and (3) isopolyacid and heteropolyacid anions: $Mo_7O_{24}^{6-}$, $V_{10}O_{28}^{6-}$, $PW_{11}CuO_{39}^{6-}$, and $SiW_9V_3O_{40}^{7-}$, $H_nA^n$ is a source of an intercalated anion in the layered double hydroxide, and n represents the charge number of the anions and is an integer of 1~7, wherein the product is made is $(1-x)M^{2+}(OH)_2+xM^{3+}(OH)_3+x/nH_nA+(m-x)H_2O \rightarrow [M^{2+}_{1-x}M^{3+}_x(OH)_2]A^{n-}_{x/n} \cdot mH_2O$; and reacting the contents in the reactor to obtain the layered double hydroxide with $A^{n-}$ as the intercalated anion.

2. The method according to claim 1, wherein:

$M^{2+}$ represents one or two divalent cations selected from $Mg^{2+}$, $Zn^{2+}$, $Ca^{2+}$ and $Ni^{2+}$, and $M^{3+}$ represents one or two trivalent cations selected from $Al^{3+}$ and $Fe^{3+}$; and $A^{n+}$ is one selected from $Cl^-$, $NO_3^-$, $CO_3^{2-}$, $SO_3^{2-}$, $PO_4^{3-}$, terephthalate, succinate, benzoate and $Mo_7O_{24}^{6-}$.

3. The method according to claim 1, wherein the reactor is a reactor fitted with a reflux device, and the contents in the reactor are reacted under stirring for 1~10 days.

4. The method according to claim 1, wherein the reactor is an airtight reactor fitted with a mixer, and the contents in the reactor are reacted under stirring for 0.1~3 days at a temperature of 100~300° C. and a pressure of 0.1~10 MPa.

* * * * *